(12) United States Patent
Cameron et al.

(10) Patent No.: US 6,894,058 B1
(45) Date of Patent: May 17, 2005

(54) USE OF 3-HYDROXY-3-METHYLGUTARYL COENZYM A REDUCTASE INHIBITORS FOR THE MANUFACTURE OF A MEDICAMENT FOR THE TREATMENT OF DIABETIC NEUROPATHY

(75) Inventors: Norman E. Cameron, Aberdeen (GB); Mary A. Cotter, Aberdeen (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/889,409

(22) PCT Filed: Feb. 1, 2000

(86) PCT No.: PCT/GB00/00280

§ 371 (c)(1),
(2), (4) Date: Feb. 22, 2002

(87) PCT Pub. No.: WO00/45818

PCT Pub. Date: Aug. 10, 2000

(30) Foreign Application Priority Data

Feb. 6, 1999 (GB) .............................................. 9902591
Feb. 6, 1999 (GB) .............................................. 9902594

(51) Int. Cl.[7] .................... A61K 31/505; A61K 31/425; A61K 31/155

(52) U.S. Cl. ....................... 514/275; 514/369; 514/635; 514/866

(58) Field of Search ................................ 514/275, 369, 514/866

(56) References Cited

U.S. PATENT DOCUMENTS

| 5,130,333 | A | 7/1992 | Pan et al. |
| 5,190,970 | A | 3/1993 | Pan et al. |
| 5,298,497 | A | 3/1994 | Tschollar et al. |
| 6,103,742 | A | 8/2000 | Ikeda et al. |
| 6,121,295 | A | 9/2000 | Ikeda et al. |
| 6,169,100 | B1 | 1/2001 | Ikeda et al. |
| 6,262,076 | B1 * | 7/2001 | Cameron et al. ........... 514/316 |
| 6,337,327 | B1 * | 1/2002 | Tuffin et al. ............. 514/226.5 |
| 6,384,062 | B1 | 5/2002 | Ikeda et al. |
| 6,448,280 | B1 * | 9/2002 | Carey et al. ................. 514/381 |

FOREIGN PATENT DOCUMENTS

| EP | 0 457 514 B1 | 11/1991 |
| EP | 0 459 453 A2 | 12/1991 |
| EP | 0 482 498 A2 | 4/1992 |
| EP | 0 521 471 A1 | 1/1993 |
| EP | 0 738 512 A1 | 10/1996 |
| WO | WO 95/13063 | 5/1995 |
| WO | WO 95/26188 | 10/1995 |
| WO | WO 97/37688 | 10/1997 |
| WO | WO 99/11260 | 3/1999 |

OTHER PUBLICATIONS

Budavari et al., The Merck Index, Twelfth Edition (1996), p. 1282, abstract No. 7605.*
Apfel, "Introduction to Diabetic Neuropathy", Excerpta Medica, Inc., 1999, p. 1S.
Vinik, "Diabetic Neuropathy: Pathogenesis and Therapy", Excerpta Medica, Inc., 1999, pp. 17S–26S.
Parry, "Management of Diabetic Neuropathy", Excerpta Medica, Inc., 1999, pp. 27S–33S.
Simons et al., "Effects of atorvastatin monotherapy and simvastatin plus cholestyramine on arterial endothelial function in patients with severe primary hypercholesterolaemia", Atherosclorisis, vol. 137, 1998, pp. 197–203.
Watts et al., "Impaired endothelium–dependent and independent dilation of forearm resistance arteries in men with diet–treated non–insulin–dependent diabetes: roles of dyslipidaemia", Clinical Science, vol. 91, 1996, pp. 567–573.
Mullen et al., "Atorvastatin But not L–Arginine Improves Endothelial Function in Type I Diabetes Mellitus: A Double–Blind Study", Journal of American College of Cardiology, vol. 56, No. 2, Aug., 2000, pp. 410–416.
Sheu, Letter, Diabetes Care, Col. 22, No. 7, Jul. 1999, pp. 1224–1225.
Evans et al., "Ciprofibrate Therapy Improves Endothelial Function and Reduces Postprandial Lipernia and Oxidative Stress in Type 2 Diabetes Mellitus", Circulation, Apr. 18, 2000, pp. 1773–1779.
Kamata et al., "Preservation of endothelium–dependent relaxation in cholesterol–fed and streptozotocin–induced diabetic mice by the chronic administration of cholestyramine", British Journal of Pharmacology, vol. 118, 1996, pp. 385–391.
McClellan et al., "Candesartan Cilexetil A Review of its Use in Essential Hypertension", Drugs, 1998, pp. 847–869.
Graham–Smith et al., "Oxford Handbook on Clinical Pharmacology and Pharmacology", Moscow, "Meditsina" 2000, part 10 (Partial Translation).
Balabolkin, "Endicrinology", Moscow, "Universum Publishing" 1998, pp 427–430 and 420–421 (Partial Translation).
Small Medical Encyclopedia, Moscow "Meditsina", 199 pp. 110 (Partial Translation).

* cited by examiner

Primary Examiner—Kevin E. Weddington
(74) Attorney, Agent, or Firm—Morgan, Lewis & Bockius LLP

(57) ABSTRACT

The present invention relates to a new use of a statin drug in the improvement of diabetic neuropathy, specifically in improving nerve conduction velocity and nerve blood flow in patients suffering diabetes, in particular to pharmaceutical combinations of the statin drug and other agents known to improve diabetic neuropathy such as an aldose reductase inhibitor (ARI), an angiotensin converting enzyme (ACE) inhibitor or an angiotensin II (AII) antagonist which combinations are useful in the prevention and treatment of the complications of diabetes.

10 Claims, No Drawings

USE OF 3-HYDROXY-3-METHYLGUTARYL COENZYM A REDUCTASE INHIBITORS FOR THE MANUFACTURE OF A MEDICAMENT FOR THE TREATMENT OF DIABETIC NEUROPATHY

This application is the National Phase of International Application PCT/GB00/00280 filed Feb. 1, 2000 which designated the U.S. and that International Application was published under PCT Article 21(2) in English.

The present invention relates to a new use of a statin drug in the improvement of diabetic neuropathy, specifically in improving nerve conduction velocity and nerve blood flow in patients suffering diabetes, in particular to pharmaceutical combinations of the statin drug and other agents known to improve diabetic neuropathy such as an aldose reductase inhibitor (ARI), an angiotensin converting enzyme (ACE) inhibitor or an angiotensin II (AII) antagonist which combinations are useful in the prevention and treatment of the complications of diabetes.

3-Hydroxy-3-methylglutaryl Coenzyme A (HMG Co A) reductase inhibitors effectively inhibit cholesterol synthesis in the liver through stimulation of the low density lipoprotein (LDL) receptors. These drugs are currently pre-eminent in the treatment of all hypercholesterolaemia, except the relatively rarely occurring homozygous familial hypercholesterolaemia. Therapy with HMG Co A-reductase inhibitors may result in regression of atherosclerotic vascular lesions and several HMG Co A-reductase inhibitors have proven to reduce mortality. Various HMG Co A-reductase inhibitors are marketed, and are collectively referred to as 'statins'.

We have discovered that statin drugs, in particular (E)-7-[4-(4-fluorophenyl)-6-isopropyl-2-[methyl(methylsulfonyl)amino]pyrimidin-5-yl](3R,5S)-3,5-dihydroxyhept-6-enoic acid or a pharmaceutically acceptable salt thereof (the AGENT), the calcium salt of which is shown in FIG. 1 below, and atorvastatin produce an improvement in the nerve conduction velocity (NCV) and nerve blood flow in an animal model of diabetic neuropathy. Therefore, statin drugs may be used to improve diabetic neuropathy, whether in type I or type II diabetes.

Therefore we present as a first feature of the invention a method for treating neuropathy in a patient suffering from diabetes comprising administering to the patient a statin drug.

As a preferred feature of the invention we present a method for improving nerve conduction velocity and/or nerve blood flow in a patient suffering diabetic neuropathy comprising administering to the patient a statin drug.

Further features of the invention include use of a statin drug in the preparation of a medicament for use in the treatment of any of the conditions mentioned above.

Examples of statin drugs include, for example, pravastatin (PRAVACHOL™), lovastatin (MEVACOR™), simvastatin (ZOCOR™), cerivastatin (LIPOBAY™), fluvastatin (LESCOL™), atorvastatin (LIPITOR™) and the AGENT, the structures of which are shown in FIG. 1. Preferably the statin drug is atorvastatin or the AGENT. Preferably the AGENT is used at a dose of 5 to 80 mg per day.

The AGENT is disclosed in European Patent Application, Publication No. 0521471, and in Bioorganic and Medicinal Chemistry, (1997), 5(2), 437444 as an inhibitor of 3-hydroxy-3-methylglutaryl CoA reductase (HMG-CoA reductase). Preferably the calcium salt is used as illustrated in FIG. 1.

Atorvastatin is disclosed in U.S. Pat. No. 5,273,995; lovastatin is disclosed in U.S. Pat. No. 4,231,938; simvastatin is disclosed U.S. Pat. No. 4,450,171 and U.S. Pat. No. 4,346,227; pravastatin is disclosed in U.S. Pat. No. 4,346,227; fluvastatin is disclosed in U.S. Pat. No. 4,739,073; cerivastatin is disclosed in U.S. Pat. No. 5,177,080 and U.S. Pat. No. 5,006,530.

Other compounds which have inhibitory activity against HMG-CoA reductase can be readily identified by using assays well known in the art. Examples of such assays are disclosed in U.S. Pat. No. 4,231,938 at column 6 and WO84/02131 at pages 30–33.

It will be appreciated that the statin drug may be administered in accordance with the invention in combination with other drugs used for treating diabetes or the complications of diabetes, such as neuropathy, nephropathy, retinopathy and cataracts. Examples of such treatments include insulin sensitising agents, insulin and oral hypoglycaemics (these are divided into four classes of drug—sulfonylureas, biguanides, prandial glucose regulators and alpha-glucosidase inhibitors). Examples of insulin sensitising agents include, for example, troglitazone, rosiglitazone, pioglitazone, MCC-555, (S)-2-ethoxy-3-[4-(2-{4-methanesulfonyloxyphenyl}ethoxy)phenyl]propanoic acid and 3-{4-[2-(4-tert-butoxycarbonylaminophenyl)ethoxy]phenyl}-(S)-2-ethoxy propanoic acid. Examples of sulfonylureas are glimepiride, glibenclamide, gliclazide, glipizide, gliquidone and tolazamide. An example of a biguanide is metformin. An example of an alpha-glucosidase inhibitor is acarbose. An example of a prandial glucose regulator is repaglinide.

Other treatments are known also to improve NCV in diabetic neuropathy and as such these represent preferred combinations of the invention. Examples of such treatments include aldose reductase inhibitors, ACE inhibitors and AII antagonists.

The use of aldose reductase inhibitors or ACE inhibitors in improving NCV and treating diabetic neuropathy is disclosed in PCT/GB98/01959. The use of AII antagonists in improving NCV and treating diabetic neuropathy is disclosed in WO93/20816.

Suitable aldose reductase inhibitors include, for example, epalrestat, tolrestat, ponolrestat, zopolrestat, AD-5467, SNK-860, ADN-138, AS-3201, zenarestat, sorbinil, methosorbinil, imirestat and minalrestat (WAY-121509).

Suitable ACE inhibitors include, for example, benazepril, benazeprilat, captopril, delapril, fentiapril, fosinopril, imidopril, libenzapril, moexipril, pentopril, perindopril, pivopril, quinapril, quinaprilat, ramipril, spirapril, spiraprilat, trandolapril, zofenopril, ceronapril, enalapril, indolapril, lisinopril, alacepril, and cilazapril. A preferred ACE inhibitor includes, for example, lisinopril, or a pharmaceutically acceptable salt thereof.

Suitable AII antagonists include, for example, losartan, irbesartan, valsartan and candesartan. A preferred AII antagonist is candesartan.

Independent aspects of the present invention include a pharmaceutical combination comprising any one of the statin drugs identified above, preferably the AGENT or atorvastatin, and any one of the named ACE inhibitors identified above, or anyone of the aldose reductase inhibitors identified above, or any one of the AII antagonists identified above. Accordingly, further independent aspects of the present invention include the following:

(1) A pharmaceutical combination comprising the AGENT and lisinopril;
(2) A pharmaceutical combination comprising atorvastatin and lisinopril;
(3) A pharmaceutical combination comprising fluvastatin and lisinopril;

(4) A pharmaceutical combination comprising pravastatin and lisinopril;

(5) A pharmaceutical combination comprising cerivastatin and lisinopril;

(6) A pharmaceutical combination comprising the AGENT and candesartan;

(7) A pharmaceutical combination comprising the AGENT, or atorvastatin, and (S)-2-ethoxy-3-[4-(2-{4-methanesulfonyloxyphenyl}ethoxy)phenyl]propanoic acid or 3-{4-[2-(4-tert-butoxycarbonylaminophenyl) ethoxy]phenyl}-(S)-2-ethoxy propanoic acid.

The 'pharmaceutical combination' may be achieved by dosing each component drug of the combination to the patient separately in individual dosage forms administered together or sequentially. Alternatively the 'pharmaceutical combination' may be together in the same unit dosage form.

Therefore, as a further aspect of the invention we represent a pharmaceutical composition comprising a pharmaceutical combination as described herein above together with a pharmaceutically acceptable carrier and/or diluent.

Independent aspects of the present invention include a pharmaceutical composition comprising any one of the statin drugs identified above, preferably the AGENT or atorvastatin, and any one of the named ACE inhibitors identified above, or any one of the aldose reductase inhibitors identified above, or any one of the AII antagonists identified above together with a pharmaceutically acceptable carrier and/or diluent. Accordingly, farther independent aspects of the present invention include the following:

(1) A pharmaceutical composition comprising the AGENT and lisinopril;

(2) A pharmaceutical composition comprising atorvastatin and lisinopril;

(3) A pharmaceutical composition comprising fluvastatin and lisinopril;

(4) A pharmaceutical composition comprising pravastatin and lisinopril;

(5) A pharmaceutical composition comprising cerivastatin and lisinopril;

(6) A pharmaceutical composition comprising AGENT and candesartan; and (7) A pharmaceutical composition comprising the AGENT, or atorvastatin, and (S)-2-ethoxy-3-[4-(2-{4-methanesulfonyloxyphenyl}ethoxy)phenyl]propanoic acid or 3-{4-[2-(4-tert-butoxycarbonylaminophenyl) ethoxy]phenyl}-(S)-2-ethoxy propanoic acid; and together with a pharmaceutically acceptable carrier and/or diluent.

A preferred pharmaceutical composition of the invention comprises the AGENT or atorvastatin and an ACE inhibitor (including any one of the ACE inhibitors specifically named above, in particular lisinopril), together with a pharmaceutically acceptable carrier and/or diluent.

A preferred pharmaceutical composition of the invention comprises the AGENT or atorvastatin and an aldose reductase inhibitor (including any one specifically named above), together with a pharmaceutically acceptable carrier and/or diluent.

A preferred pharmaceutical composition of the invention comprises the AGENT or atorvastatin and an AII antagonist (including any one specifically named above and preferably candesartan), together with a pharmaceutically acceptable carrier and/or diluent.

The pharmaceutical compositions of the present invention may be administered in a standard manner for example by oral or parenteral administration, using conventional systemic dosage forms, such as a tablets, capsules, pills, powders, aqueous or oily solutions or suspensions, emulsions, sterile injectable aqueous or oily solutions or suspensions. These dosage forms will include the necessary carrier material, excipient, lubricant, buffer, bulking agent, antioxidant, dispersant or the like. In particular, compositions for oral administration are preferred.

The dose of a statin drug, an aldose reductase inhibitor, an AII antagonist or an ACE inhibitor which can be administered in accordance with the present invention depends on several factors, for example the age, weight and the severity of the condition under treatment, as well as the route of administration, dosage form and regimen and the desired result, and additionally the potency of the statin drug, aldose reductase inhibitor, AII antagonist and ACE inhibitor employed in the composition. In addition, account should be taken of the recommended maximum daily dosages for the ACE inhibitors.

Prolonged administration of an ACE inhibitor at a therapeutically effective dose may be deleterious or give rise to side effects in certain patients, for example it may lead to significant deterioration of renal function, induce hyperkalemia, neutropenia, angioneurotic oedema, rash or diarrhoea or give rise to a dry cough. Administration of an ARI may also give rise to deleterious effects or side effects at the dose required to inhibit the enzyme aldose reductase sufficiently to produce a significant beneficial therapeutic effect. The present invention lessens the problems associated with administration of an ARI or an ACE inhibitor alone and/or provides a means for obtaining a therapeutic effect which is significantly greater than that otherwise obtainable with the single agents when administered alone. Furthermore, diabetic neuropathy involve a complex mechanism or number of mechanisms, which initiate a cascade of biochemical alterations that in turn lead to structural changes. These may result in a diverse patient population. The present invention therefore provides the additional advantage that it allows tailoring of treatment to the needs of a particular patient population.

The combination of a statin, preferably atorvastatin or the AGENT, with and ACE inhibitor, preferably lisinopril, is either additive or synergistic in effect in the treatment of neuropathy, in particular NCV or nerve blood flow, in diabetic pateients.

The combination of a statin, preferably atorvastatin or the AGENT, with and AII antagonist, preferably candesartan, is either additive or synergistic in effect in the treatment of neuropathy, in particular NCV or nerve blood flow, in diabetic pateients.

A unit dosage formulation such as a tablet or capsule will usually contain, for example, from 1 mg to 100 mg of the statin drug, or/and from 0.1 mg to 500 mg of an aldose reductase inhibitor, or/and from 0.1 mg to 500 mg of an ACE inhibitor. Preferably a unit dose formulation will contain 5 to 80 mg of the statin drug, or/and 0.1 to 100 mg of an aldose reductase inhibitor, or/and 0.1 mg to 100 mg of an AII antagonist or/and 0.1 to 100 mg of an ACE inhibitor.

The present invention covers the pharmaceutical combination of (or product containing) the statin and an aldose reductase inhibitor, an AII antagonist or an ACE inhibitor for simultaneous, separate or sequential use in the treatment of diabetic neuropathy. In one aspect of the present invention, the AGENT drug and the aldose reductase inhibitor or AII antagonist or ACE inhibitor is presented in admixture in one pharmaceutical dosage form. In another aspect, the present invention covers the administration of separate unit dosages of the AGENT and aldose reductase inhibitor or AII antagonist or ACE inhibitor in order to achieve the desired therapeutic effect. Such separate unit dosages may be administered concurrently or sequentially as determined by the clinician. The present invention also covers an agent for the treatment of diabetic neuropathy comprising a pharmaceutically acceptable carrier and/or diluent and, as active agents, a statin drug, preferably the AGENT or atorvastatin, and an aldose reductase inhibitor or an AII antagonist or an ACE inhibitor in quantities producing a synergistic therapeutic effect.

In another aspect of the invention there is provided a combination of pharmaceutical compositions for combination therapy of diabetic neuropathy, the combination consisting of a pharmaceutical composition comprising the statin drug and a pharmaceutical composition comprising an aldose reductase inhibitor or a pharmaceutical composition comprising an AU antagonist or a pharmaceutical composition comprising an ACE inhibitor.

A further aspect of the present invention comprises the use of a statin drug and an aldose reductase inhibitor or an AII antagonist or an ACE inhibitor in the preparation of a pharmaceutical composition for use in the treatment of diabetic neuropathy.

A further aspect of the present invention is a method for treating diabetic neuropathy wherein a therapeutically effective amount of a statin drug in combination with an aldose reductase inhibitor or an AII antagonist or an ACE inhibitor is administered systemically, such as orally or parenterally. Where the patient to be treated is normotensive, the ACE inhibitor or AII antagonist will preferably be administered in amounts below that required to cause a reduction in blood pressure. Where the patient to be treated is hypertensive, the ACE inhibitor or AII antagonist will preferably be used in amounts usually employed to treat hypertension.

The effect of a pharmaceutical composition of the present invention may be examined by using one or more of the published models of diabetic neuropathy well known in the art. The pharmaceutical compositions of the present invention are particularly useful for the prevention of, reducing the development of, or reversal of, deficits in nerve function found in diabetic patients, and therefore particularly useful in the treatment of diabetic neuropathy. This may be demonstrated, for example, by measuring markers such as nerve conduction velocity, nerve blood flow, nerve evoked potential amplitude, quantitative sensory testing, autonomic function testing and morphometric changes. Experimentally, studies analogous to those described in Diabetologia, 1992, Vol. 35, pages 12–18 and 1994, Vol. 37, pages 651–663 may be carried out.

A further aspect of the present invention is a method of treating or preventing the development of disease conditions associated with impaired neuronal conduction velocity in a warm-blooded animal (including a human being) requiring such treatment comprising administering to said animal a therapeutically effective amount of a pharmaceutical combination or composition as described above.

A further aspect of the present invention is a method of reversing impaired neuronal conduction velocity in a warm-blooded animal (including a human being) requiring such treatment comprising administering to said animal a therapeutically effective amount of a pharmaceutical combination or composition as described above.

Dosages of the AGENT may be administered according to the cholesterol lowering effect desired from a range of 5–80 mg per day in any number of unit dosages.

Suitable dosages of the statins, ACE inhibitors, aldose reductase inhibitors or AII antagonists mentioned herein are those which are available commercially, and which may be further reduced as suggested herein, or as advised in such publications as Monthly Index of Medical Specialities (P.O. BOX 43, Ruislip, Middlesex, UK).

The following non-limiting Examples serve to illustrate the present invention.

EXAMPLE 1

Suitable pharmaceutical compositions of an aldose reductase inhibitor (ARI) include the following:

|  | mg/tablet |
|---|---|
| Tablet 1 | |
| ARI | 100 |
| Lactose Ph. Eur. | 182.75 |
| Croscarmellose sodium | 12.0 |
| Maize starch paste (5% w/v paste) | 2.25 |
| Magnesium stearate | 3.0 |
| Tablet 2 | |
| ARI | 50 |
| Lactose Ph. Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| Tablet 3 | |
| ARI | 1.0 |
| Lactose Ph. Eur. | 93.25 |
| Croscarmellose sodium | 4.0 |
| Maize starch paste (5% w/v paste) | 0.75 |
| Magnesium stearate | 1.0 |
| Capsule 1 | |
| ARI | 10 |
| Lactose Ph. Eur. | 488.5 |
| Magnesium stearate | 1.5 |

EXAMPLE 2

Suitable pharmaceutical compositions of an ACE inhibitor include the following:

| Tablet 1 | |
|---|---|
| ACE Inhibitor | 100 |
| Corn starch | 50 |
| Gelatin | 7.5 |
| Microcrystalline cellulose | 25 |
| Magnesium stearate | 2.5 |
| Tablet 2 | |
| ACE inhibitor | 20 |
| Pregelatinised starch | 82 |
| Microcrystalline cellulose | 82 |
| Magnesium stearate | 1 |

EXAMPLE 3

| Capsule | mg |
|---|---|
| The AGENT | 5.0 |
| Lactose | 42.5 |
| Corn starch | 20.0 |
| Microcrystalline cellulose | 32.0 |
| Pregelatinised starch | 3.3 |
| Hydrotalcite | 1.1 |
| Magnesium stearate | 1.1 |

Capsules containing 1, 2.5 or 10 mg of the Agent may be obtained similarly using more or less lactose as appropriate., to achieve a fill weight of 105 mg.

EXAMPLE 4

Suitable pharmaceutical compositions containing the AGENT and an ACE inhibitor in a single dosage form include the following:

| Capsule | mg |
| --- | --- |
| The AGENT | 5.0 |
| Lisinopril | 10.0 |
| Lactose | 42.5 |
| Corn starch | 20.0 |
| Microcrystalline cellulose | 32.0 |
| Pregelatinised starch | 3.3 |
| Hydrotalcite | 1.1 |
| Magnesium stearate | 1.1 |

EXAMPLE 5

A patient requiring treatment for diabetic neuropathy is treated with the AGENT (10 mg) and lisinopril (10 mg). Lisinopril is administered twice daily and the AGENT is administered once daily.

EXAMPLE 6

Male Sprague-Dawley rats, 19 weeks old at the start of the study, were divided into non-diabetic animals (normal control group) and animals rendered diabetic by intraperitoneal administration of streptozotocin, (40–45 mg/kg, freshly dissolved in sterile saline). Diabetes was verified 24 hours later by estimating hyperglycaemia and glucosuria (Visidex II and Diastix; Ames, Slough, UK). Diabetic rats were tested weekly and weighed daily. Animals were rejected if the plasma glucose concentration was <20 mM of if body weight consistently increased over 3 days. Samples were taken from the tail vein or carotid artery after final experiments for plasma glucose determination (GOD-Perid method; Boehringer Mannheim, Mannheim, Germany). After 6 weeks of untreated diabetes, groups of rats were treated for a further 2 weeks with the AGENT, dissolved in the drinking water.

At the end of the treatment period, rats were anaesthetised with thiobutabarbitone by intraperitoneal injection (50–100 mg/kg). The trachea was cannulated for artificial ventilation and a carotid cannula was used to monitor mean systemic blood pressure.

Motor nerve conduction velocity was measured (as previously described by Cameron et al, Diabetologia, 1993, Vol. 36, pages 299–304) between sciatic notch and knee in the nerve branch to tibialis anterior muscle, which is representative of the whole sciatic nerve in terms of susceptibility to diabetes and treatment effects.

Sensory conduction velocity in saphenous nerve was measured between the groin and ankle (as previously described by Cameron et al. Quarterly Journal of Experimental Physiology, 1989, vol. 74, pages 917–926).

Sciatic blood flow was measured by hydrogen clearance microelectrode polarography (as described by Cameron et al., Diabetologia, 1994, vol. 37, pages 651–663). The nerve was exposed between the sciatic notch and the knee and the skin around the incision was sutured to a metal ring to form a pool that was filled with paraffin oil that was maintained at 35–37° C. by radiant heat. A glass-insulated platinum microelectrode was inserted into the middle portion of the sciatic nerve and polarised at 250 mV with respect to a subcutaneous reference microelectrode. 10% Hydrogen was added to the inspired gas, the proportions of nitrogen and oxygen being adjusted to 70% and 20% respectively. When the hydrogen current recorded by the electrode had stabilised, indicating equilibrium with arterial blood, the hydrogen supply was shut off and nitrogen supply was increased appropriately. The hydrogen clearance curve was recorded until a baseline, defined as no systematic decline in electrode current over 5 minutes. To estimate blood flow, clearance curves were digitised and exponential curves were fitted to the data by computer using non-linear regression. The best fitting exponent gave a measure of nerve blood flow.

Data

All data expressed as group mean±SEM (number of rats used in brackets)

| Sciatic Nerve Motor Conduction Velocity | |
| --- | --- |
| Control Values | |
| Non-diabetical control | 64.04 ± 0.46 (10) |
| 8 week diabetic + vehicle | 50.35 ± 0.93 (6) |
| Atorvastatin | |
| 9Diabetic + 2 weeks of dosing at 20 mg/kg | 61.53 ± 0.76 (6) |
| Diabetic + 2 weeks of dosing at 50 mg/kg | 63.59 ± 0.69 (6) |
| The AGENT | |
| Diabetic + 2 weeks of dosing at 20 mg/kg Dose response determination 5 groups of 8 rats - dose ranged from 0.3–20 mg/kg - $ED_{50}$ = 2.3 mg/kg | 63.34 ± 0.61 (8) |

| Saphenous Nerve Sensory Conduction Velocity | |
| --- | --- |
| Control Values | |
| Non-diabetic control | 61.09 m/s ± 0.67 (10) |
| 8 week diabetic + vehicle | 52.77 m/s ± 0.79 (6) |
| Atorvastatin | |
| Diabetic + 2 weeks of dosing at 20 mg/kg | 59.77 m/s ± 0.93 (6) |
| Diabetic + 2 weeks of dosing at 50 mg/kg | 60.72 m/s ± 0.94 (6) |
| The AGENT | |
| Diabetic + 2 weeks of dosing at 20 mg/kg Dose response determination 5 groups of 8 rats - dose ranged from 0.3–20 mg/kg - $ED_{50}$ = 0.9 mg/kg | 60.57 m/s ± 0.83 (8) |

| Sciatic Nerve Blood Flow | |
| --- | --- |
| Control Values | |
| Non-diabetic control | 17.89 ml/min/100 g (of nerve tissue) ± 0.65 (10) |
| 8 week diabetic + vehicle | 8.82 ml/min/100 g ± 0.56 (10) |
| Atorvastatin | |
| Diabetic + 2 weeks of dosing at 50 mg/kg | 16.96 ± 1.39 ml/min/100 g (6) |
| The AGENT | |
| Diabetic + 2 weeks of dosing at 20 mg/kg | 16.19 ± 0.51 ml/min/100 g (8) |

FIG. 1

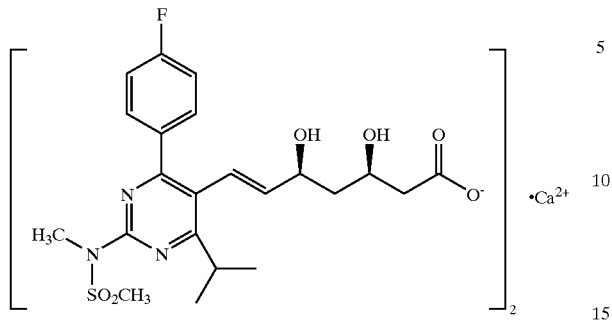

The AGENT

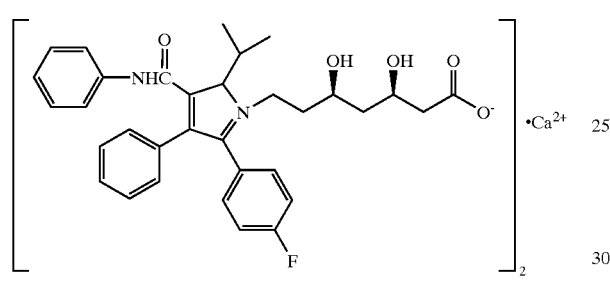

Atorvastatin

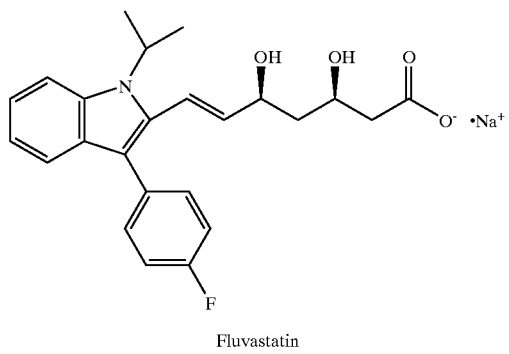

Fluvastatin

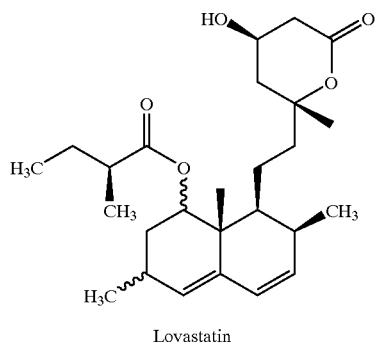

Lovastatin

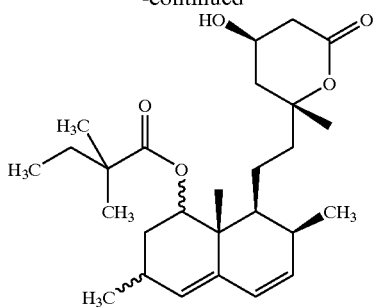

Simvastatin

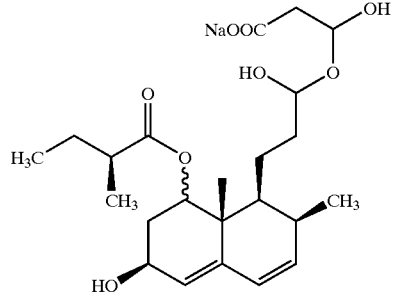

Pravastatin

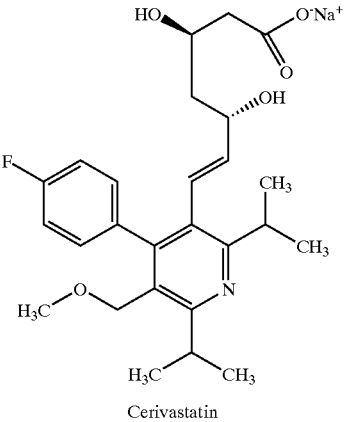

Cerivastatin

What is claimed is:

1. A method for treating diabetic neuropathy in a warm blooded animal in need thereof comprising administering to said animal a treatment-effective amount of the statin drug (E)-7-[4-(4-fluorophenyl)-6-isopropyl-2-[methyl (methylsulfonyl)amino]pyrimidin-5-yl](3R,5S)-3,5-dihydroxyhept-6-enoic acid or a pharmaceutically acceptable salt thereof.

2. A method as claimed in claim 1 wherein the statin drug is the calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid.

3. The method as claimed in claim 1 or 2 wherein the statin drug is administered as a pharmaceutical combination additionally comprising at least one other drug used for treating diabetes or the complications of diabetes.

4. The method as claimed in claim 3 wherein the at least one other drug used for treating diabetes or the complications of diabetes is selected from insulin, troglitazone, rosiglitazone, pioglitazone, MCC-555, (S)-2-ethoxy-3-[4-(2-{4-methanesulfonyloxyphenyl}ethoxy)phenyl]propanoic acid and 3-{4-[2-(4-tert-butoxycarbonylaminophenyl) ethoxy]phenyl}-(S)-2-ethoxy propanoic acid, glimepiride, glibenclamide, gliclazide, glipizide, gliquidone and tolazamide, metformin, acarbose and repaglinide.

5. A method as claimed in claim 3 wherein the at least one other drug used for treating diabetes or the complications of diabetes is an insulin sensitising agent.

6. A method as claimed in claim 5 wherein the insulin sensitising agent is (S)-2-ethoxy-3-[4-(2-{4-methanesulfonyloxyphenyl}ethoxy)phenyl]propanoic acid.

7. A method as claimed in claim 3 wherein the drugs are administered separately in individual dosage forms together or sequentially.

8. A method as claimed in claim 3 wherein the drugs are administered in the same unit dosage form.

9. A method as claimed in claim 1 or 2 wherein 5 mg to 80 mg of the statin drug is administered.

10. A method as claimed in claim 3 wherein the drugs are administered orally.

* * * * *